US00PP10697P

United States Patent [19]

McGredy

[11] Patent Number: Plant 10,697

[45] Date of Patent: Nov. 24, 1998

[54] HYBRID TEA ROSE PLANT NAME 'MACCHOPSU'

[75] Inventor: Sam McGredy, Auckland, New Zealand

[73] Assignee: DeVor Nurseries, Inc., Watsonville, Calif.

[21] Appl. No.: 742,142

[22] Filed: Oct. 31, 1996

[51] Int. Cl.[6] ..... A01H 5/00

[52] U.S. Cl. ..... Plt./20

[58] Field of Search ..... Plt./20, 21

[56] References Cited

U.S. PATENT DOCUMENTS

P.P. 4,391 3/1979 Delbard ..... Plt./20

*Primary Examiner*—Howard J. Locker
*Attorney, Agent, or Firm*—Christie, Parker & Hale, LLP

[57] ABSTRACT

A hybrid tea rose variety producing red flowers.

1 Drawing Sheet

BACKGROUND OF THE INVENTION

The present invention relates to a new and distinct hybrid tea rose variety which was originated by my crossing as seed parent the variety known as 'Louise Gardner' and as pollen parent the variety known as 'Mme. Delbard', U.S. Plant Pat. No. 4,391. The varietal denomination of this new rose is 'Macchopsu'.

SUMMARY OF THE INVENTION

Among the novel characteristics possessed by this new variety which distinguish it from its parents and all other varieties of which I am aware are its attractive red flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison with Parents

'Macchopsu' has an orange cast whereas 'Mme Delbard' is a true scarlet red. In addition, 'Macchopsu' is a much freer blooming plant than 'Mme Delbard'. 'Louise Gardner' is a yellow blend, small-flowered hybrid tea producing flowers in small trusses while 'Macchopsu' produces flowers more singly and whereas 'Macchopsu' has glossy green foliage, 'Louise Gardner' has matte grey-green foliage.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Louise Gardner'.

*Pollen parent.*—'Mme. Delbard' (U.S. Plant Pat. No. 4,391).

Class: Hybrid Tea.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming Habit: Continuous.

A. Bud:

(1) *Size.*—Medium about 4 cm long to 3 cm wide at widest point.

(2) *Form.*—Pointed.

(3) *Color.*—When sepals first divide, bud color is near 45B.

(4) *Sepals.*—Longer than bud, spread when bloom opens and reflex as bloom ages; some sepals are foliaceous with leaf shaped ends; sepals about 3 cm to 4 cm; color near 143C with near 183A in center and at base. Color: Near 143C with near 183A in center; undersurface near 144A in center and near 144C at tip and at base.

(5) *Peduncle.*—Length: About 7.5 cm to about 9.5 cm. Aspect: Hairy, some prickles. Strength: Erect, sturdy. Color: Near 144A with shading near 183A.

(6) *Bracts.*—About 1 or 2, elliptical, about 7 to 9 cm below flower base, near 146A.

B. Bloom:

(1) *Size.*—Average size when fully expanded — about 8 cm to about 10 cm.

(2) *Borne*—Singly.

(3) *Form.*—Imbricated, cupped, becoming ruffled at maturity.

(4) *Petalage.*—Number of petals under normal conditions — about 32 to 36.

(5) *Color* (⅓–½ *open*).—Outer petals — Top surface: Near 45B. Undersurface: Near 45C. Inner petals—Top surface: Near 45A. Undersurface: Near 45C. Base of petals: Near 150B. General tonality from a distance: Red.

(6) *Color (Fully open*).—Outer petals — Top surface: Near 44A. Undersurface: Near 42B. Inner petals—Top surface: Near 46B. Undersurface: Near 42B. Base of petals: Near 145D. General tonality from distance: Red.

(7) *Color change.*—Color lightens slightly. Petal top surface Near 44A. Petal undersurface Near 52B. General tonality at a distance Red.

C. Petals:
(1) *Texture.*—Thick and smooth.
(2) *Appearance.*—Inside velvety and outside matte.
(3) *Form.*—Orbicular with ruffled edging.
(4) *Arrangement.*—Imbricated.
(5) *Petaloids.*—Few, about 2 or 3.
(6) *Fragrance.*—None.
(7) *Lasting quality.*—On plant about 4 to 6 days, about 8 to 12 days after cutting.
(8) *Persistence.*—Petals drop off cleanly.

Reproductive Organs

A. Stamens
(1) *Arrangements.*—Irregularly arranged around styles.
(2) *Anthers.*—Color near 15B.
(3) *Filament.*—Near 60C.
(4) *Pollen.*—Color — near 15B.
B. Pistils:
(1) *Styles.*—Bunched.
(2) *Stigmas.*—Color near 22C.
C. Characteristics of hips: Not observed to date.

Plant

A. Form: Upright, first season, about 120 cm to 140 cm height; about 85 cm to 115 cm wide.
B. Growth: Vigorous.
C. Foliage: Compound 3 to 5 leaflets.
(1) *Size.*—Medium, leaflets about 14 cm to 16 cm long, about 11 to 13 cm wide.
(2) *Quantity.*—Abundant.
(3) *Color.*—New foliage — upper side near 183A underside near 183B; mature foliage — upper side near 146A underside near 146B.
(4) *Shape.*—Ovate.
(5) *Texture.*—Upper side — leathery, glossy; underside — leathery, veiny.
(6) *Edge.*—Serrate.
(7) *Serration.*—Denticulate.
(8) *Leaf stem.*—Color — medium green.
(9) *Stipules.*—Parallel, adnate, slightly bearded.
(10) *Rachis.*—Smooth with occasional prickles.
(11) *Petioles.*—Top near 146B, underside near 144C.
(12) *Auricle.*—Curving outwardly and slightly downwards.
(13) *Resistance to disease.*—Good resistance to blackspot, mildew and rust.
D. Wood:
(1) *New wood.*—Color near 183A, bark smooth.
(2) *Old wood.*—Color near 144A, bark smooth.
E. Flower stem: About 20 cm to about 28 cm from last cut.
F. Thorns:
(1) *Thorns.*—Quantity: On main stalk, many; laterals from stalk, many. Form: Wing-shaped, slightly curved downward. Length: About 0.9 to 1 cm. Color: Near 183A when young. Position: Irregular.
(2) *Prickles.*—Some.
G. Winter hardiness: Winter hardy in Watsonville, Calif.

I claim:

1. A new and distinct variety of hybrid tea rose plant variety, substantially as shown and described.

* * * * *

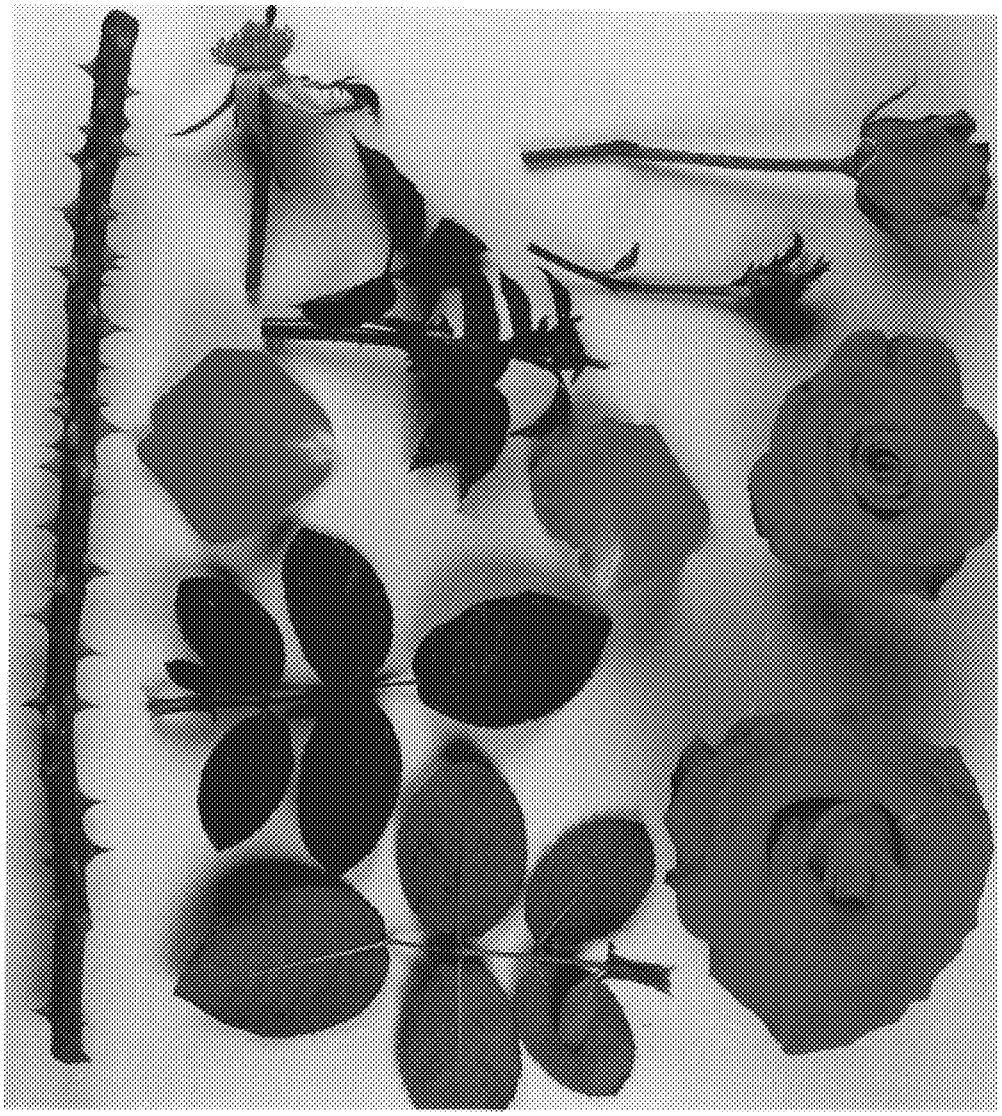

UNITED STATES PATENT AND TRADEMARK OFFICE

CERTIFICATE OF CORRECTION

PATENT NO. : Plant 10,697
DATED : November 24, 1998
INVENTOR(S) : Sam McGredy

It is certified that error appears in the above-identified patent and that said Letters Patent is hereby corrected as shown below:

On the title page item [54], and column 1, change "NAME" to -- NAMED --.
Column 3, line 30, change "16 cm" to -- 16+ cm --.

Signed and Sealed this
Fourth Day of January, 2000

*Attest:*

*Attesting Officer*

*Acting Commissioner of Patents and Trademarks*